(12) United States Patent
Vasos et al.

(10) Patent No.: US 8,362,770 B2
(45) Date of Patent: Jan. 29, 2013

(54) METHOD FOR NUCLEAR MAGNETIC RESONANCE (NMR) SPECTROSCOPY MEASUREMENTS USING LONG-LIVED COHERENCES (LLC)

(75) Inventors: Paul Romeo Vasos, Lausanne (CH); Riddhiman Sarkar, Prilly (CH); Puneet Ahuja, Lausanne (CH); Geoffrey Bodenhausen, Paris (FR)

(73) Assignees: Bruker BioSpin AG, Faelladen (CH); Ecole Polytechnique Fédérale de Lausanne, Laussane (CH)

( * ) Notice: Subject to any disclaimer, the term of this patent is extended or adjusted under 35 U.S.C. 154(b) by 462 days.

(21) Appl. No.: 12/662,724

(22) Filed: Apr. 30, 2010

(65) Prior Publication Data

US 2011/0001477 A1    Jan. 6, 2011

(30) Foreign Application Priority Data

Jul. 3, 2009  (EP) .................................... 09164544

(51) Int. Cl.
*G01V 3/00*    (2006.01)
(52) U.S. Cl. ........................................................ 324/309
(58) Field of Classification Search ........... 324/300–322
See application file for complete search history.

(56) References Cited

U.S. PATENT DOCUMENTS
5,001,427 A    3/1991  Fujiwara

OTHER PUBLICATIONS

Sarkar et al., Long-Lived Coherences for Homogeneous Line Narrowing in Spectroscopy, Physical Review Letters 104, 053001 (2010).*

M. Carravetta, O.G. Johannessen + M.H. Levitt, "Beyond the $T_1$ limit: Singlet nuclear spin states in low magnetic fields", Phys. Rev. Lett. 92, 153003 (2004).
M. Carravetta + M.H. Levitt, "Long-lived nuclear spin states in high-field solution NMR", J. Am. Chem. Soc. 126,6228-6229 (2004).
R. Sarkar, P.R. Vasos + G. Bodenhausen, "Singlet-State Exchange NMR Spectroscopy for the Study of Very Slow Dynamic Processes", J.Am.Chem. Soc. 129, 328-334 (2007).
G. Pileio, M. Carravetta, E. Hughes + M.H. Levitt, "The long-lived nuclear singlet state of N-15-nitrous oxide in solution", J. Am. Chem. Soc. 130, 12582-12583 (2008).
M. H. Levitt, G. Pileio + M. Carravetta, "Nuclear Singlet States in Solution NMR", (2009).
K. Pervushin, R. Riek, G. Wider + K. Wuthrich, "Attenuated T-2 relaxation by mutual cancellation of dipole-dipole coupling and chemical shift anisotropy indicates an avenue to NMR structures of very large biological macromolecules in solution", Proc. Nat. Acad. Sci. 94, 12366-12371 (1997).
R. Sprangers + L.E. Kay, "Quantitaive dynamics and binding studies of the 205 proteasome by NMR", Nature 445, 618-622 (2007).
G. Pileio + M.H. Levitt, "J-Stabilisation of singlet states in the solution NMR of multiple-spin systems", J.Magn. Reson. 187, 141-145 (2007).

(Continued)

*Primary Examiner* — Melissa Koval
*Assistant Examiner* — Daniel Miller
(74) *Attorney, Agent, or Firm* — Paul Vincent

(57) ABSTRACT

A method for nuclear magnetic resonance (NMR) spectroscopy of a sample comprises preparation of the sample and carrying out an NMR spectroscopy measurement. Preparation includes excitation of long lived coherences (LLC) between the singlet state $S_0$ and the central triplet state $T_0$ of nuclei of the sample. The thermal equilibrium Boltzmann distribution ($I_z+S_z$) is thereby transformed into a difference ($I_z-S_z$), which is flipped to the transverse plane, and irradiation of the sample with an rf-field is initiated. The LLC is sustained by maintaining the rf-irradiation during an interval $t_1$ and the LLC is converted into observable magnetisation by interrupting the rf-irradiation. The method allows nuclear magnetic resonance spectroscopy measurements with improved spectral resolution.

9 Claims, 2 Drawing Sheets

OTHER PUBLICATIONS

P. Ahuja, R. Sarkar, P.R. Vasos + G. Bodenhausen, "Long lived states in multiple-spin systems", Chemphyschem, 10, 2217-2220 (2009).

R. Sarkar, P. Ahuja, D. Moskau, P.R. Vasos + G. Bodenhausen, "Extending the scope of singlet-state spectroscopy", ChemPhysChem 8, 2652-2656 (2007).

K. Gopalakrishnan + G. Bodenhausen, "Lifetimes of singlet-states under coherent off-resonance irradiation in NMR spectroscopy", J.Magn. Reson. 182, 254-259 (2006).

P. Ahuja, R. Sarkar, P.R. Vasos + G. Bodenhausen, "Molecular Properties Determined from the Relaxation of Long-Lived Spin States", J.Chem. phys. 127, 134112 (2007).

G. Pileio, M. Concistré, M. Carravetta + M.H. Levitt, "Long-lived nuclear spin states in the solution NMR of four-spin systems", J. Magn. Reson 182, 353-357 (2006).

E. Vinogradov + A.K. Grant, "Long-lived states in solution NMR: Selection rules for intramolecular dipolar relaxation in low magnetic fields", J.Magn. Reson. 188, 176-182 (2007).

S.A. Smith, T.O. Levant, B.H. Meier + R.R. Ernst, "Computer-Simulations in Magnetic-Resonance—an Object-Oriented Programming Approach", J.Magn.Reson.Ser.A 106, 75-105 (1994).

D.Marion + K. Wuthrich, "Application of Phase Sensitive Two-Dimensional Correlated Spectroscopy (Cosy) for Measurements of H-1-H-1 Spin-Spin Coupling-Constants in Proteins", Biochem. Biophys Res. Comm. 113, 967-974 (1983).

V. Tugarinov, P. M. Hwang, J.E. Ollerenshaw, L. E. Kay, "Cross-Correlated Relaxation Enhanced $^1$H-$^{13}$C NMR Spectroscopy of Methyl Groups in Very High Molecular Weight Proteins and Protein Complexes" J. Am. Chem. Soc. 125, 10420-10428 (2003).

\* cited by examiner

METHOD FOR NUCLEAR MAGNETIC RESONANCE (NMR) SPECTROSCOPY MEASUREMENTS USING LONG-LIVED COHERENCES (LLC)

This application claims Paris Convention priority to EP 09 164 544.0 filed Jul. 3, 2009 the entire disclosure of which is hereby incorporated by reference.

BACKGROUND OF THE INVENTION

The invention concerns a method for nuclear magnetic resonance (NMR) spectroscopy of a sample comprising preparation of the sample and carrying out an NMR spectroscopy measurement. A method as described above is known from reference 8.

It has been shown recently[1,2] that it is possible to excite and sustain long-lived states (LLS) in systems comprising at least two coupled spins I=S=½. These LLS correspond to a difference between the populations of the anti-symmetric singlet state $S_0=N(|\alpha\beta\rangle-|\beta\alpha\rangle)$ (where $N=2^{-1/2}$) and the mean population of the three symmetric triplet states $T_{+1}=|\alpha\alpha\rangle$, $T_0=N(|\alpha\beta\rangle+|\beta\alpha\rangle)$, and $T_{-1}=|\beta\beta\rangle$. In order to sustain LLS, the spins must be rendered magnetically equivalent, either by removing the sample from the magnetic field, or by applying a suitable radio-frequency (rf) field. Typically, a continuous rf irradiation with an amplitude $\omega_1=\gamma B_1$, using an rf carrier placed half-way between the two chemical shifts, $\omega_{RF}=(\omega_1-\omega_S)/2$ can sustain LLS. These LLS correspond to diagonal elements of the matrix representation of the Liouvillian that describes the time-evolution in the presence of the rf field. Because the eigenvalues $\lambda_{LLS}=R_{LLS}=1/T_{LLS}$ are real, the LLS relax mono-exponentially without oscillations. The lifetimes $T_{LLS}$ of LLS can be much longer than the spin-lattice relaxation time ($T_{LLS} \gg T_1$), in favourable cases as much as a 36 times longer[3]. Spin polarisation has been preserved for tens of minutes using LLS in nitrous oxide[4].

ELF Experiments

Levitt and co-workers discussed the behaviour of coherent superpositions of symmetric and antisymmetric states in a slightly different context than the present invention. In their ingenious experiments, the Zeeman polarized sample was taken out of the magnetic field, which in our language brings about a transformation from the product base into singlet-triplet base. In a vanishing magnetic field, it is possible to bring about a Rabi nutation of the two-level system comprising the $S_0$ and $T_0$ states by irradiation with an electromagnetic field at extremely low frequency (ELF)[5], typically on the order of a few tens of Hz. In the case of $^{15}N_2O$, they determined the scalar coupling $J(^{15}N, ^{15}N)$ with unparalleled accuracy, since the linewidths are on the order of a few mHz, and the corresponding lifetimes on the order of 100 s.

'Transverse Relaxation Optimized Spectroscopy' (TROSY)

Wüthrich and co-workers made significant progress in improving the spectral resolution by seeking to extend the lifetimes of coherences. Their idea, which has become known under the acronym TROSY (for Transverse Relaxation Optimised Spectroscopy), was to use the mutual cancellation (negative interference) between the dipole-dipole (DD) and chemical shift anisotropy (CSA) interactions to trim relaxation rates[6]. In rapidly rotating side-chain methyl protons, there are similar beneficial interference effects between dipolar interactions[7]. The TROSY method has brought the threshold of molecular sizes up to which NMR is useful for structural biology of single-domain proteins from ca. 20 kDa to ca. 50 kDa. The use of selective deuteration techniques can help to further extend lifetimes of single-quantum coherences, since the number of dipolar interactions between the observed nuclei and other spins with high gyromagnetic ratios is reduced and, therefore, the remaining nuclei have slower relaxation rates. The combination of TROSY with selective deuteration has increased the molecular weight threshold considerably: recently, an NMR analysis of the dynamics in the 670 kDa 20S proteasome core particle was reported[8].

Bio-NMR

The main strengths of nuclear magnetic resonance (NMR) lie in its atomic resolution and its non-invasive nature. To extract information from different sites the signals have to be resolved, i.e., have a frequency separation larger than their linewidth. As the linewidths are proportional to the decay rate constant of the observed spin coherence, the above requirement amounts to creating spin coherences with slow relaxation rates. This has been one of the main goals of liquid-state NMR spectroscopists for the last decade, ever since it was established that this would allow us to analyse more complicated molecules.

Object of the invention is to further improve spectral resolution in nuclear magnetic resonance sperocopy measurements.

SUMMARY OF THE INVENTION

This object is achieved by a method according to the independent claim.

The preparation of the inventive method comprises the following steps:
(a) excitation of long lived coherences (LLC) between the singlet state $S_0$ and the central triplet state $T_0$ of nuclei of the sample, whereby
  (i) the thermal equilibrium Boltzmann distribution ($I_z+S_z$) is trans-formed into a difference ($I_z-S_z$),
  (ii) ($I_z-S_z$) is flipped to the transverse plane, and
  (iii) irradiation of the sample with an rf-field is initiated;
(b) sustaining of the LLC by maintaining the rf-irradiation during an interval $t_1$,
(c) conversion of the LLC into observable magnetisation by interrupting the rf-irradiation.

A long lived coherence (LLC) is a coherent superposition between the singlet and the central triplet state of nuclei of a kind. ($I_z-S_z$) mentioned in step (i) is the difference of z-components of spin operators S and I of nuclei, and describes a quantum mechanic state of said nuclei. By flipping ($I_z-S_z$) to the transverse plane in step (ii) ($I_x-S_x$) or ($I_y-S_y$) is excited respectively. The rf-irradiation is applied during the interval $t_1$. By initiating the rf-irradiation in step (iii) the before excited ($I_x-S_x$) or ($I_y-S_y$) respectively is converted into $Q_{LLC}$, whereby $Q_{LLC}$ is an operator which represents the LLC. The LLC are sustained as long as rf-irradiation is applied. By interrupting rf-irradiation LLC is converted into observable magnetisation immediately, whereby "observable magnetisation" means magnetisation which is detectable by MR measurements (transverse magnetisation). The rf-irradiation is preferably carried out along an x-axis, if the $Q_{LLC}$ contains ($I_x-S_x$) terms and along the y-axis if the $Q_{LLC}$ contains ($I_y-S_y$) terms, whereby the x-axis and the y-axis each are perpendicular to the z-direction.

The inventive preparation is carried out in a magnetic field, in particular in the magnetic field of the NMR magnet.

It is shown that coherent superpositions of antisymmetric and symmetric states that are referred to as long-lived coherences (LLC's) can be excited and sustained by a coherent radio-frequency (rf) irradiation in high-resolution nuclear magnetic resonance (NMR) in isotropic solution. The coherent radio-frequency (rf) irradiation may be weak, i.e, less than 1 kHz If relaxation is due predominantly to the dipolar interaction between the active spins, the life-times of LLC's are significantly longer than the transverse relaxation times $T_2$ of single-quantum coherences ($3 < T_{LLC}/T_2 < 9$), depending on the correlation time of rotational diffusion. The life-times of LLC's are generally shorter than the lifetimes of the populations of long-lived states LLS ($T_{LLC} < T_{LLS}$) in the same system. Unlike LLS that decay monoexponentially, the oscillatory time-dependence of LLC's is governed by scalar couplings. These oscillations can be mapped out point-by-point in the manner of two-dimensional spectroscopy. The Fourier transformations of these oscillations yield spectra with very high resolution, with half-widths at half-height $\Delta v_{LLC} = (\pi T_{LLC})^{-1} \ll \Delta v = (\pi T_2)^{-1}$. In this work, linewidths $\Delta v_{LLC} = 0.6$ Hz were observed in two-spin systems belonging to mobile terminal glycine aminoacids in the protein Ubiquitin, where single-quantum linewidths are typically $\Delta v = 1.6$ Hz.

The rf-field is preferably a continuous wave rf-field.

In a highly preferred variant the thermal equilibrium Boltzmann distribution ($I_z + S_z$) is transformed into a difference ($I_z - S_z$) by applying a semi-selective π pulse.

In order to achieve extreme narrow line width it is further advantageous to apply a ($\pi/2$) pulse in step (ii). In case of excitation of ($I_x - S_x$) a ($\pi/2$)$_y$ pulse is applied, in case of exciting or ($I_y - S_y$) a ($\pi/2$)$_x$ pulse is applied.

In a special variant of the inventive method least two semi-selective IT pulses are applied either simultaneously or consecutively in order to excite ($I_z - S_z$) of different kinds of nuclei of the sample, and in step (ii) a single ($\pi/2$) pulse is applied. Thus LLC of different kinds of nuclei can be excited.

The NMR spectroscopy measurement is preferably a 2D NMR spectroscopy measurement. In case of a 2D NMR spectroscopy measurement the rf-irradiation during $t_1$ is repeated whereby $t_1$ is varied for each repetition. Time-proportional phase increments (TPPI) are used to build the indirect dimension. A 2D experiment can for example use 128 transients and a relaxation delay of 2 s.

The advantages of the inventive method are shown best when the NMR spectroscopy measurement is a liquid-state NMR measurement, in particular carried out in isotropic solution.

The invention is shown in the drawing:

DESCRIPTION OF THE PREFERRED EMBODIMENT

The present invention focuses on elements, in particular off-diagonal elements, of the Liouvillian matrix that describes the evolution of a suitably prepared two spin-½ system subjected to a preferably continuous rf field[9-12]. A coherent superposition between the singlet and central triplet states can be readily defined in the singlet-triplet base[3]:

$$Q_{LLC} = |S_0\rangle\langle T_0| \qquad (1)$$

These will henceforth be called long-lived coherences (LLC). In terms of products of Cartesian operators in the product base, these may also be written:

$$Q_{LLC} = \frac{1}{2}(I_x - S_x) + i\frac{1}{2}(I_y S_z - I_z S_y) \qquad (2)$$

These coherences evolve under complex eigenvalues of the Liouvillian:

$$\frac{d}{dt} Q_{LLC} = -(R_{LLC} + i 2\pi J_{IS}) Q_{LLC} \qquad (3)$$

The imaginary part leads to oscillations that are determined by the scalar coupling $J_{IS}$, while the decay of the coherence is governed by $R_{LLC}$. A counterpart with an opposite oscillation frequency $-J_{IS}$ will be discussed elsewhere. As shown below, the lifetime $T_{LLC} = 1/R_{LLC}$ is usually significantly longer than the transverse relaxation times $T_2$ of the single-quantum coherences, i.e., $T_{LLC} \gg T_2$.

Figure 1:
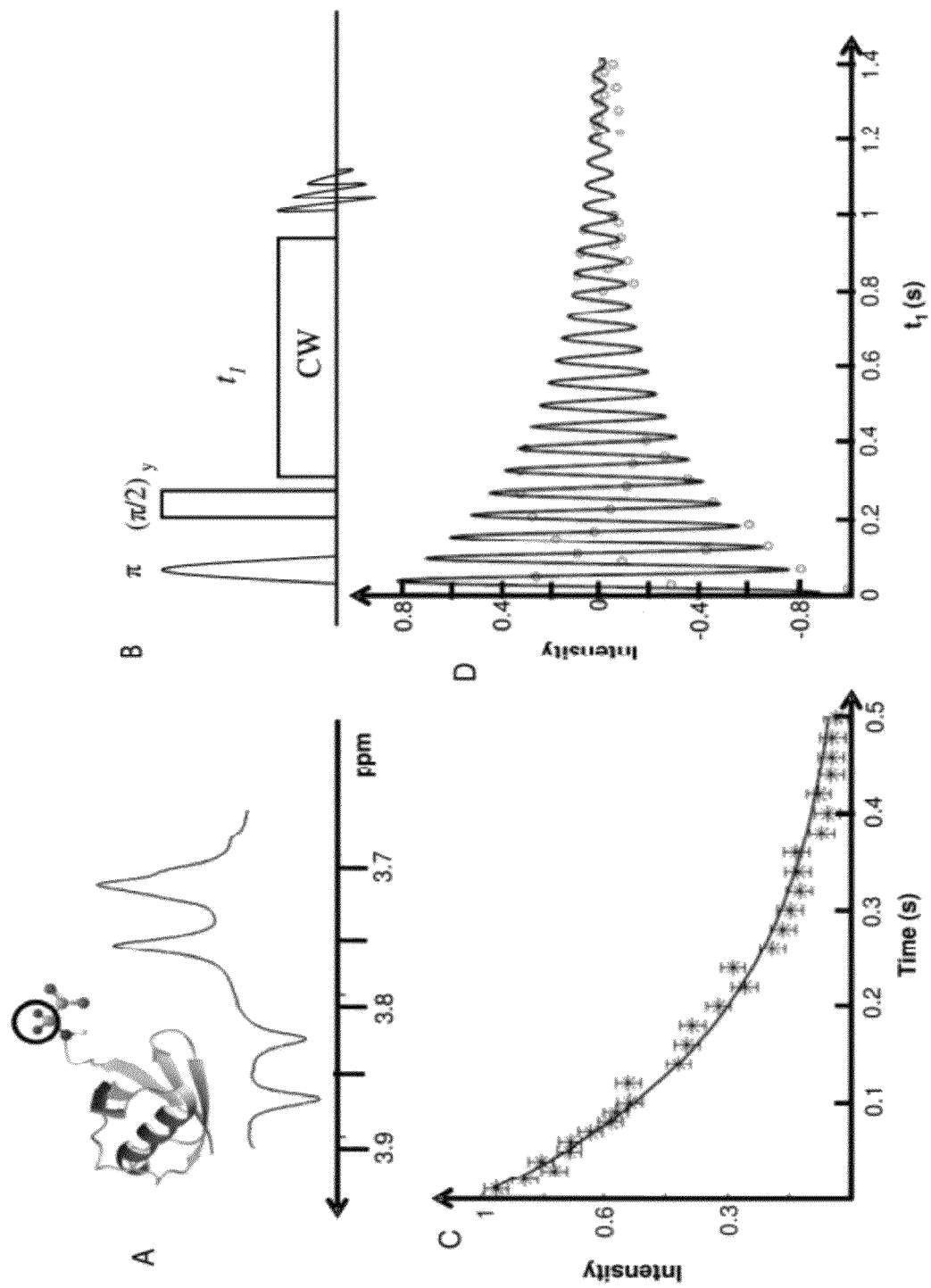
FIG. 1A shows a Proton spectrum of a 2 mM solution of the protein Ubiquitin (insert) obtained at 400 MHz and 300 K using the pulse sequence shown in FIG. 1B with $t_1 = 120$ ms, showing signals of the diastereotopic protons $H_1^\alpha$ and $H_2^\alpha$ of Gly-76 (circled) with $J_{IS} = -17.17$ Hz.
FIG. 1B shows a pulse sequence used to create long-lived coherences and convert them back into observable single-quantum coherences.
FIG. 1C shows an experimental $T_{1\rho}$ decay of single-quantum coherences that are spin-locked by continuous-wave (cw) rf irradiation, yielding the relaxation rate constant $R_{1\rho} = 1/T_{1\rho}$.
FIG. 1D shows an oscillating signal due to the long-lived coherence obtained using the sequence shown in FIG. 1B, plotted as a function of the evolution time $t_1$ and fitted to a function $I(t_1) = I_0 \cos(2\pi J_{IS} t_1) \exp(-R_{LLC} t_1)$. The best fit parameters are $J_{IS} = -17.17 \pm 0.08$ Hz and $R_{LLC} = 2.5 \pm 0.7$ s$^{-1}$.

The coherent and relaxation properties of LLC can be utilised to record very high-resolution 2D spectra, notably in order to measure J-couplings with high precision or to resolve nearly-degenerate signals. In order to excite LLC, one can transform the thermal equilibrium Boltzmann distribution ($I_z + S_z$) into a difference ($I_z - S_z$). An example for a simple pulse sequence is shown in FIG. 1B, where one of the two doublets in the spectrum is inverted by a semi-selective π pulse. Next, a ($\pi/2$)$_y$ pulse is applied to excite ($I_x - S_x$), followed by continuous-wave (CW) rf irradiation along the x-axis. This perturbation in effect suppresses the chemical shifts, so that the system is best described in the singlet-triplet basis. In the process, the difference ($I_x - S_x$) is converted into $Q_{LLC}$. The quantum yield of this conversion is 100%. The LLC is sustained by rf irradiation and the real component of the complex coherence is measured by switching the rf field off after a variable evolution time $t_1$ in the manner of two-dimensional spectroscopy.

If only the effect of the dipolar interaction between two protons I and S is considered, the transverse relaxation rate of the single-quantum coherences in a weakly-coupled two-spin systems is described by $$R_2 = \left(\frac{b_{IS}^2}{20}\right)[9J(0) + 15J(\omega) + 6J(2\omega)] \quad (4)$$

with the spectral density functions $$J(\omega) = \frac{\tau_c}{1 + \omega^2 \tau_c^2},$$

and where $$b_{IS} = -\frac{\mu_0}{4\pi}\frac{\gamma^2 \hbar}{r_{IS}^3}$$

is the strength of the homonuclear dipolar coupling between two spins I and S, $r_{IS}$ is the distance between them, $\tau_c$ is the rotational correlation time of the molecule, and the other quantities have their usual meaning. On the other hand, it can be shown[13, 14] that the LLC decay rate is given by:

$$R_{LLC} = \left(\frac{b_{IS}^2}{20}\right)[J(0) + 3J(\omega) + 6J(2\omega)] \quad (5)$$

Hence, the LLC is predicted to have longer lifetimes than single-quantum coherences in all motional regimes, i.e., for arbitrary molecular tumbling rates, as long as the dipolar coupling between the spins is the predominant interaction. The ratio is $R_{LLC}/R_2 = 1/3$ in the fast-tumbling limit $\tau_c \ll 1/\omega_0$, when the spectral densities are equal at all frequencies, and $R_{LLC}/R_2 = 1/9$ in the spin diffusion limit (slow tumbling, $\tau_c \gg 1/\omega_0$), when only the spectral densities at zero frequency remain significant. In terms of lifetimes, this implies that the ratio varies in the range $3 < T_{LLC}/T_2 < 9$. Extraneous relaxation mechanisms such as the dipolar interaction with spins outside the pair on which LLC is excited will tend to reduce the advantage. The modulation of the chemical shift anisotropy (CSA) of the spins will also have a deleterious effect on the relaxation time constants of the LLC, except in favourable cases, when it has the same spin-exchange symmetry as the dipole-dipole interaction between the two coupled spins[14].

The decay rates of LLC have been experimentally determined and compared with the decay rates of the single-quantum coherences associated with the two diastereotopic protons $H_1^\alpha$ and $H_2^\alpha$ of Gly-76 in the mobile C-terminal part of the protein Ubiquitin. Numerical simulations assuming pure dipolar relaxation predict a relaxation rate $R_{LLC}=2.3$ s$^{-1}$. The relaxation rate constants measured in the experiments shown in FIGS. 1C and D are $R_{LLC}=2.5\pm0.7$ s$^{-1}$ and $R_{1\rho} \approx R_2 = 5.6\pm0.1$ s$^{-1}$, so that the experimental ratio is $R_{LLC}/R_2=0.46$ or $T_{LLC}/T_2=2.17$.

The Fourier transform of the oscillations yields the magnitude of the $J_{IS}$ coupling with very high accuracy, since the linewidth is determined by the relaxation rate $R_{LLC}$. To this effect, 2D experiments were performed with the pulse sequence of FIG. 1B. In FIG. 2, a 2D spectrum is shown where the chemical shifts are seen in the direct $\omega_2$ dimension, whereas only one frequency, which corresponds to the $J_{IS}$ coupling constant, is detected in the $\omega_1$ dimension. By increasing the time increment $\Delta t_1$, one can adequately sample the oscillations up to a long $t_1^{max}$ to catch the signal until it has decayed completely. Undersampling leads to spectral aliasing, but since there is only one peak in the indirect dimension, it is easy to correct for this effect. The 2D spectrum in FIG. 2B was recorded by undersampling in the $\omega_1$ dimension, recording 220 points with increments $\Delta t_1=50$ ms, so that the spectral width in the $\omega_1$ dimension was 10 Hz and $t_1^{max}=11$ s. The full linewidth at half-height of the signal was found to be $\Delta v_{1/2}=0.6$ Hz in the $\omega_1$ dimension.

Figure 2A:
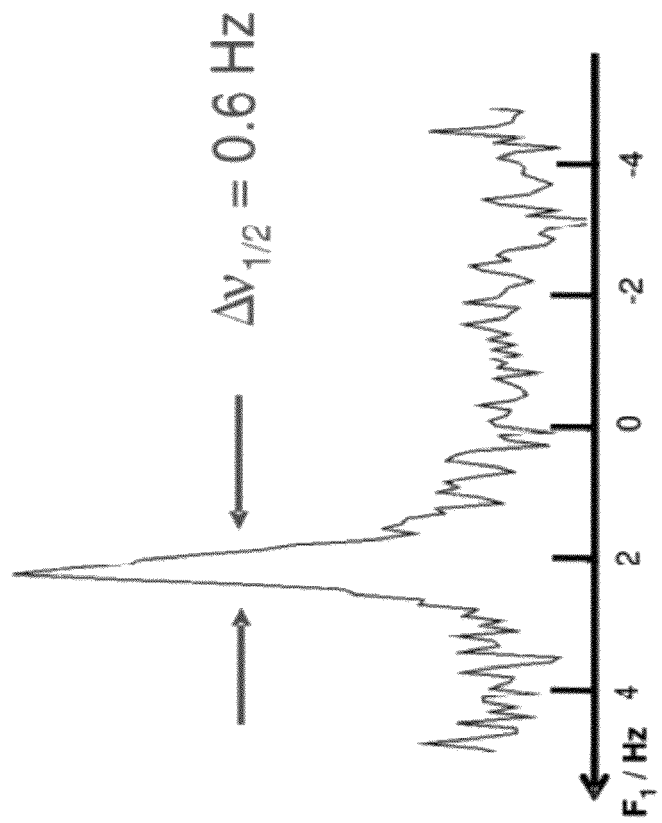
FIG. 2A shows a 2D spectrum of the LLC of the two protons $H_1^\alpha$ and $H_2^\alpha$ of Gly-76 in Ubiquitin (insert) obtained with a spectral width reduced to 10 Hz in the $\omega_1$ dimension, so that the folded peaks appear at ($\omega_1 = 2.17$ Hz. All 2D spectra were obtained using TPPI.
Figure 2B:
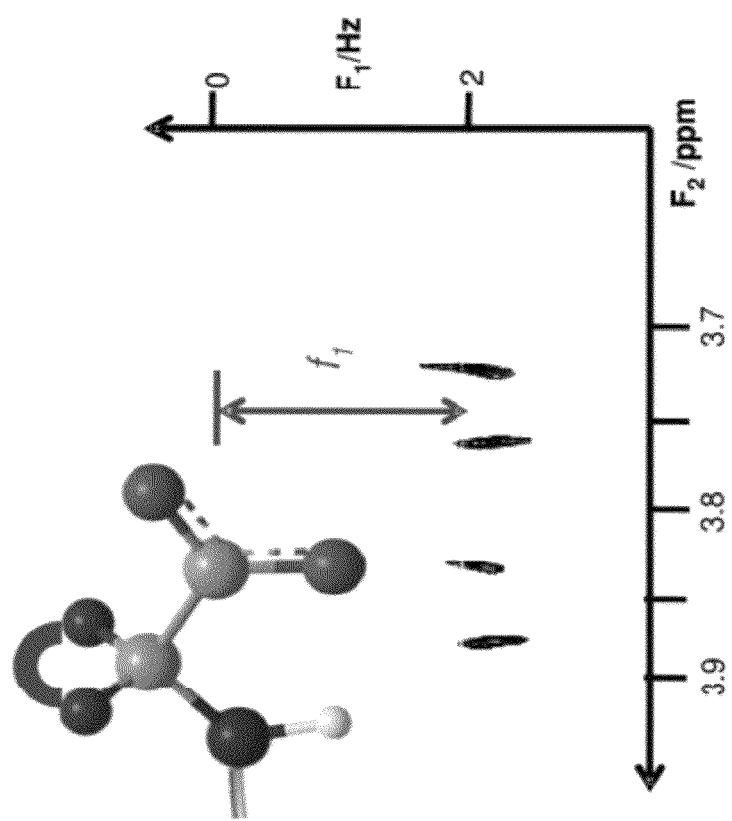
FIG. 2B shows a cross-section was extracted from the spectrum shown in FIG. 2A at $\omega_2 = 3.84$ ppm; the linewidth in the $\omega_1$ dimension is 0.6 Hz.

Since the coupling constant $J_{IS}$ between the two geminal protons $H_{1\alpha}$ and $H_2^\alpha$ of Glycine is known to be in the vicinity of 17 Hz, it is clear that the signal appearing at 2.17 Hz in the spectrum in FIG. 2A must be folded three times, so that the true value is $J_{IS}=-17.17$ Hz.

In conclusion, long-lived coherences offer a means of reducing linewidths much below the usual limits of NMR spectroscopy. This opens the way for 2D spectroscopy with very well-resolved peaks in the indirect dimension and improved sensitivity. The method can be used for spectral editing and assignment. As for LLS[10, 15, 16], it may turn out to be possible to excite and sustain LLC in groups involving more than two coupled spins.

The Numerical simulations have been performed using the package GAMMA[17] by subjecting an initial state defined by an operator $(I_x-S_x)$ to a Liouvillian including continuous rf irradiation and dipolar relaxation and describing the evolution by means of the Liouville-von Neumann equation. A spin system consisting of four spins was considered (two aliphatic protons in each of the two residues Gly-75 and Gly-76 in the relatively mobile C-terminal loop of Ubiquitin), with spin interactions modulated at an effective correlation time $\tau_c=2$ ns.

Ubiquitin with a natural isotopic distribution was dissolved in $D_2O$ to a concentration of 2 mM. The 2D spectra were acquired at T=300 K and $B_0=4.9$ T (400 MHz), using time-proportional phase increments[18] (TPPI) in the indirect dimension. The amplitude of the continuous-wave rf irradiation was $v_1=1.9$ kHz. Each 2D experiment used 128 transients and a relaxation delay of 2 s. A semi-selective Gaussian $\pi$ pulse of 30 ms duration was used to invert the doublet of one of the two spins.

REFERENCES

M. Carravetta, O. G. Johannessen & M. H. Levitt. Beyond the $T_1$ limit: Singlet nuclear spin states in low magnetic fields. *Phys. Rev. Lett.* 92, 153003 (2004).
2. M. Carravetta & M. H. Levitt. Long-lived nuclear spin states in high-field solution NMR. *J. Am. Chem. Soc.* 126, 6228-6229 (2004).
3. R. Sarkar, P. R. Vasos & G. Bodenhausen. Singlet-State Exchange NMR Spectroscopy for the Study of Very Slow Dynamic Processes. *J. Am. Chem. Soc.* 129, 328-334 (2007).
4. G. Pileio, M. Carravetta, E. Hughes & M. H. Levitt. The long-lived nuclear singlet state of N-15-nitrous oxide in solution. *J. Am. Chem. Soc.* 130, 12582-12583 (2008).
5. M. H. Levitt, G. Pileio & M. Carravetta. Nuclear Singlet States in Solution NMR. (2009).
6. K. Pervushin, R. Riek, G. Wider & K. Wuthrich. Attenuated T-2 relaxation by mutual cancellation of dipole-dipole coupling and chemical shift anisotropy indicates an avenue to NMR structures of very large biological macromolecules in solution. *Proc. Nat. Acad. Sci.* 94, 12366-12371 (1997).
7V. Tugarinov, P. M. Hwang, J. E. Ollerenshaw & L. E. Kay. Cross-correlated relaxation enhanced H-1-C-13 NMR spectroscopy of methyl groups in very high molecular weight proteins and protein complexes. *J. Am. Chem. Soc.* 125, 10420-10428 (2003).

8. R. Sprangers & L. E. Kay. Quantitative dynamics and binding studies of the 20S proteasome by NMR. *Nature* 445, 618-622 (2007).
9. G. Pileio & M. H. Levitt. J-Stabilisation of singlet states in the solution NMR of multiple-spin systems. *J. Magn. Reson.* 187, 141-145 (2007).
10. P. Ahuja, R. Sarkar, P. R. Vasos & G. Bodenhausen. Long lived states in multiple-spin systems. *Chemphyschem* in press (2009).
11. R. Sarkar, P. Ahuja, D. Moskau, P. R. Vasos & G. Bodenhausen. Extending the scope of singlet-state spectroscopy. *ChemPhysChem* 8, 2652-2656 (2007).
12. K. Gopalakrishnan & G. Bodenhausen. Lifetimes of singlet-states under coherent off-resonance irradiation in NMR spectroscopy. *J. Magn. Reson.* 182, 254-259 (2006).
13. J. Cavanagh, W. J. Fairbrother, A. G. Palmer & N. J. Skelton. Protein NMR Spectroscopy: Principles and Practice. *Elsevier Science* (1996).
14. P. Ahuja, R. Sarkar, P. R. Vasos & G. Bodenhausen. Molecular Properties Determined from the Relaxation of Long-Lived Spin States. *J. Chem. Phys.* 127, 134112 (2007).
15. G. Pileio, M. Concistré, M. Carravetta & M. H. Levitt. Long-lived nuclear spin states in the solution NMR of four-spin systems. *J. Magn. Reson.* 182, 353-357 (2006).
16. E. Vinogradov & A. K. Grant. Long-lived states in solution NMR: Selection rules for intramolecular dipolar relaxation in low magnetic fields. *J. Magn. Reson.* 188, 176-182 (2007).
17. S. A. Smith, T. O. Levante, B. H. Meier & R. R. Ernst. Computer-Simulations in Magnetic-Resonance—an Object-Oriented Programming Approach. *J. Magn. Reson. Ser. A* 106, 75-105 (1994).
18. D. Marion & K. Wuthrich. Application of Phase Sensitive Two-Dimensional Correlated Spectroscopy (Cosy) for Measurements of H-1-H-1 Spin-Spin Coupling-Constants in Proteins. *Biochem. Biophys Res. Comm.* 113, 967-974 (1983).

We claim:

1. A method for nuclear magnetic resonance (NMR) spectroscopy of a sample with which the sample is prepared and an NMR spectroscopy measurement is carried out, the method comprising the steps of:
   a) transforming a thermal equilibrium Boltzmann distribution ($I_z+S_z$) into a difference ($I_z-S_z$);
   b) flipping the difference ($I_z-S_z$) to a transverse plane;
   c) irradiating the sample with an rf-field to effect, in combination with steps a) and b), excitation of long lived coherences (LLC) between a singlet state $S_0$ and a central triplet state $T_0$ of nuclei of the sample;
   d) sustaining the LLC by maintaining rf-irradiation during an interval $t_1$; and
   e) converting the LLC into observable magnetisation by interrupting the rf-irradiation.

2. The method of claim 1, wherein the rf-field is a continuous wave rf-field.

3. The method of claim 1, wherein, in step a), the thermal equilibrium Boltzmann distribution ($I_z+S_z$) is transformed into a difference ($I_z-S_z$) by applying a semi-selective π pulse.

4. The method of claim 1, wherein, in step b), a ($\pi/2$) pulse is applied.

5. The method of claim 3, wherein, in step b), a ($\pi/2$) pulse is applied.

6. The method of claim 5, wherein, in step a) at least two semi-selective π pulses are applied either simultaneously or consecutively in order to excite ($I_z-S_z$) of different kinds of nuclei of the sample, and, in step b), a single ($\pi/2$) pulse is applied.

7. The method of claim 1, wherein the NMR spectroscopy measurement is a 2D NMR spectroscopy measurement.

8. The method of claim 1, wherein the NMR spectroscopy measurement is a liquid-state NMR measurement.

9. The method of claim 8, wherein the NMR measurement is carried out in isotropic solution.

\* \* \* \* \*

UNITED STATES PATENT AND TRADEMARK OFFICE
CERTIFICATE OF CORRECTION

PATENT NO. : 8,362,770 B2
APPLICATION NO. : 12/662724
DATED : January 29, 2013
INVENTOR(S) : Paul Romeo Vasos et al.

Page 1 of 1

It is certified that error appears in the above-identified patent and that said Letters Patent is hereby corrected as shown below:

Title page, item [73] Assignee: should read as follows:

--Bruker BioSpin AG, ~~Faelladen~~Faellanden (CH); Ecole Polytechnique Fédérale de Lausanne, ~~Laussane~~Lausanne (CH)--.

Signed and Sealed this
Twenty-sixth Day of March, 2013

Teresa Stanek Rea
*Acting Director of the United States Patent and Trademark Office*